US012558365B2

(12) United States Patent
Selker

(10) Patent No.: US 12,558,365 B2
(45) Date of Patent: Feb. 24, 2026

(54) METHODS OF TREATING ACUTE CORONARY SYNDROMES

(71) Applicant: Tufts Medical Center, Inc., Boston, MA (US)

(72) Inventor: Harry Selker, Wellesley, MA (US)

(73) Assignee: Tufts Medical Center, Inc., Boston, MA (US)

( * ) Notice: Subject to any disclaimer, the term of this patent is extended or adjusted under 35 U.S.C. 154(b) by 868 days.

(21) Appl. No.: 17/438,712

(22) PCT Filed: Mar. 12, 2020

(86) PCT No.: PCT/US2020/022250
§ 371 (c)(1),
(2) Date: Sep. 13, 2021

(87) PCT Pub. No.: WO2020/185996
PCT Pub. Date: Sep. 17, 2020

(65) Prior Publication Data
US 2022/0241303 A1 Aug. 4, 2022

Related U.S. Application Data

(60) Provisional application No. 62/817,693, filed on Mar. 13, 2019.

(51) Int. Cl.
| | |
|---|---|
| *A61K 31/7004* | (2006.01) |
| *A61K 33/14* | (2006.01) |
| *A61K 38/28* | (2006.01) |
| *A61P 9/00* | (2006.01) |

(52) U.S. Cl.
CPC .......... *A61K 31/7004* (2013.01); *A61K 33/14* (2013.01); *A61K 38/28* (2013.01); *A61P 9/00* (2018.01)

(58) Field of Classification Search
None
See application file for complete search history.

(56) References Cited

PUBLICATIONS

International Preliminary Report on Patentability for International Application No. PCT/US2020/022250, mailed Sep. 23, 2021 (8 pages).

Grossman et al., "Glucose-Insulin-Potassium Revived: Current Status in Acute Coronary Syndromes and the Energy-Depleted Heart," Circulation 127(9):1040-1048 (2013).
International Search Report and Written Opinion for PCT International Application No. PCT/US2020/022250, mailed May 26, 2020 (9 pages).
Jin et al., "Glucose-insulin-potassium therapy in patients with acute coronary syndrome: a meta-analysis of randomized controlled trials," BMC Cardiovasc. Disord. 14:169 (2014) (8 pages).
Selker et al., "Out-of-hospital administration of intravenous glucose-insulin-potassium in patients with suspected acute coronary syndromes: the IMMEDIATE randomized controlled trial," available in PMC Sep. 17, 2004 published in final edited form as: JAMA 307(18):1925-1933 (includes supplemental content) (2012) (25 pages).
Switaj et al., "Acute Coronary Syndrome: Current Treatment," Am. Fam. Phys. 95(4):232-240 (2017).
Grossman AN et al. Glucose-insulin-potassium revived: current status in acute coronary syndromes and the energy-depleted heart. 2013;127:1040-1048. PMID 23459576.
Selker HP et al. Very Early Administration of Glucose-Insulin-Potassium (GIK) by Emergency Medical Service for Acute Coronary Syndromes: Biological Mechanisms for Benefit in the IMMEDIATE Trial. Amer Heart J. 2016;178:168-175. PMID 27502865.
Selker HP et al. One-year outcomes of out-of-hospital administration of intravenous glucose, insulin and potassium (GIK) in patients with suspected acute coronary syndrome in the IMMEDIATE (Immediate Myocardial Metabolic Enhancement During Initial Assessment and Treatment in Emergency care) trial. Am J Cardiol. 2014;113 (10):1599-605 PMID 24792735; PMCID PMC4043184.
Maehara A et al. Relationship Between Infarct Size and Outcomes Following Primary PCI: Patient-Level Analysis From 10 Randomized Trials. J Am Coll Cardiol. 2016;57(14):1674-1683.
Selker HP et al. Relationship Between Therapeutic Effects on Infarct Size in Acute Myocardial Infarction and Therapeutic effects on One-year Outcomes: A Patient-Level Analysis of Randomized Clinical Trials. Am Heart J. Jun. 2017;188:18-25. PMID 28577674.
Beshansky JR et al. A community consultation survey to evaluate support for and success of the IMMEDIATE trial. Clinical Trials. 2014;11(2):178-186. PMID 24686107; PMCID PMC4025913.
Sullivan AL et al. Factors associated with longer time to treatment for patients with suspected acute coronary syndromes. Circ Cardiovasc Qual Outcomes. 2014;7:86-95. PMID 24425697; PMCID PMC3985420.
Ray M et al. A predictive model to identify patients with suspected acute coronary syndromes at high risk of cardiac arrest or in-hospital mortality: An IMMEDIATE Trial sub-study. Int J Cardiol Heart & Vasculature. 2015;9:37-42.

(Continued)

*Primary Examiner* — Dale R Miller

(74) *Attorney, Agent, or Firm* — Doreen Yatko Trujillo; VLP Law Group LLP

(57) ABSTRACT

The invention provides methods for treating and preventing acute coronary syndromes (ACS). The methods involve initiation of the administration of glucose-insulin-potassium (GIK) soon (e.g., within 3 hours) after the onset of ACS symptoms.

22 Claims, No Drawings

(56)                    References Cited

PUBLICATIONS

Ellis KL et al. Common Variants Associated with Changes in Levels of Circulating Free-Fatty Acids after Administration of Glucose-Insulin-Potassium (GIK) Therapy in the IMMEDIATE Trial. The Pharmacogenomics J. Epub Dec. 8, 2015. PMID 26644202.

Maroko PR et al. Effect of glucose-insulin-potassium infusion on myocardial infarction following experimental coronary artery occlusion. Circulation. 1972;45:1160-75.

Selker HP et al. Out-of-hospital administration of intravenous glucose-insulin-potassium in patients with suspected acute coronary syndromes: the IMMEDIATE randomized controlled trial. JAMA. May 9, 2012;307(18):1925-33. doi: 10.1001/jama.2012.426. Epub Mar. 27, 2012. PMID: 22452807; PMCID: PMC4167391.

METHODS OF TREATING ACUTE CORONARY SYNDROMES

STATEMENT AS TO FEDERALLY FUNDED RESEARCH

This invention was made with government support under grant numbers TR001609, TR001064, and TR002544 awarded by the National Institutes of Health. The government has certain rights in the invention.

FIELD OF THE INVENTION

The invention relates to methods for treating or preventing acute coronary syndromes.

BACKGROUND

Acute coronary syndromes (ACS) is a term used to describe a variety of conditions that are associated with sudden, reduced blood flow to the heart. These conditions include, for example, myocardial infarction, or heart attack, in which cell death results in damaged or destroyed heart tissue. It is also the most common cause of cardiac arrest and death. ACS often manifests as severe chest pain or discomfort. It is a medical emergency that requires prompt diagnosis and care. Treatment goals include improving blood flow, treating complications, and preventing future problems. ACS afflicts approximately 1.4 million people in the United States each year, and many more throughout the world. ACS and its sequelae thus present an enormous medical, social, and economic burden worldwide. Accordingly, there is a need for effective treatments for ACS.

SUMMARY

The invention provides methods of treating, inhibiting, or preventing acute coronary syndromes (ACS), or one or more symptoms thereof, in a patient, the methods including of initiating the administration a solution of glucose-insulin-potassium (GIK) to the patient within 0-3 hours of ACS symptom onset.

The invention also includes methods of treating, inhibiting, or preventing acute coronary syndromes (ACS), or one or more symptoms thereof, in a patient, the methods including of initiating the administration a solution of glucose-insulin-potassium (GIK) to the patient upon assessment by emergency medical service personnel.

In some embodiments, the administration of GIK is initiated upon assessment in (a) the emergency department (ED), (b) the hospital upon cardiac arrest, (c) a medical office setting, or (d) under the care of paramedics in the community.

In some embodiments, the patient has or is at risk of developing one or more ACS symptom selected from the group consisting of: chest pain, angina, radiating pain from the chest to the shoulders, arms, upper abdomen, back, neck, or jaw; nausea or vomiting; indigestion; shortness of breath; heavy sweating; lightheadedness; dizziness; fainting; unusual or unexplained fatigue; and feeling restless or apprehensive.

In some embodiments, the GIK is administered during a time frame from ACS symptom onset selected from the group consisting of 0-½ hour, ½-1 hour, 1-1½ hours, 1½-2 hours, 2-2½ hours, 2½-3 hours, 0-1 hour, ½-1½ hours, 1-2 hours, and 1½-2½ hours.

In some embodiments, the patient experiences an improvement in progression to myocardial infarction, 30-day survival, in-hospital mortality, or cardiac arrest due to the GIK treatment.

In some embodiments, the patient experiences a significant clinical improvement, or a group of patients experiences a statistically significant improvement, with respect to 30-day survival, 30-day heart failure, or in-hospital cardiac arrest.

In some embodiments, the patient is further treated with aspirin, P2Y12 receptor antagonist (e.g., Clopidogrel (Plavix), Prasugrel (Effient), and Ticagrelor (Brilinta)), anticoagulant (e.g., Bivalirudin (Angiomax), Enoxaparin (Lovenox), Fondaparinux (Arixtra), and unfractionated heparin); beta blockers (e.g., Carvedilol, oral (Coreg), Metoprolol, IV, Metoprolol, oral (Lopressor)), angiotensin-converting enzyme inhibitors (e.g., Enalapril (Vasotec), Captopril and Lisinopril), angiotensin receptor blocker (e.g., Valsartan (Diovan)), fibrinolytic agents (e.g., Tenecteplase (TNK-tPA), Reteplase (rPA), and Streptokinase), statin (e.g., Atorvastatin (Lipitor), simvastatin, and atorvastatin), morphine, nitroglycerin, oxygen, interventional angioplasty, and surgery.

In some embodiments, the GIK includes 25-35% glucose, 45-55 U/L regular insulin, and 70-90 mEq potassium chloride per liter. In some embodiments, the GIK includes 30% glucose, 50 U/L regular insulin, and 80 mEq of potassium chloride per liter.

In some embodiments, the GIK is administered at a speed of 1 to 2 mL/kg/hour for 10-14 hours. In some embodiments, the GIK is administered at a speed of 1.5 mL/kg/hour for 12 hours.

The invention further provides compositions including a solution of glucose-insulin-potassium (GIK) for use in treating, inhibiting, or preventing acute coronary syndromes (ACS) in a patient, wherein administration of the GIK is initiated within 0-3 hours of ACS symptom onset.

The invention also includes compositions including a solution of GIK for use in treating, inhibiting, or preventing acute coronary syndromes (ACS) in a patient, wherein administration of the GIK is initiated upon assessment by emergency medical service personnel.

In some embodiments, the administration of GIK is initiated upon assessment in (a) the emergency department (ED), (b) the hospital upon cardiac arrest, (c) a medical office setting, or (d) under the care of paramedics in the community.

In some embodiments, the patient has or is at risk of developing one or more ACS symptom selected from the group consisting of: chest pain, angina, radiating pain from the chest to the shoulders, arms, upper abdomen, back, neck, or jaw; nausea or vomiting; indigestion; shortness of breath; heavy sweating; lightheadedness; dizziness; fainting; unusual or unexplained fatigue; and feeling restless or apprehensive.

In some embodiments, the GIK is administered during a time frame from ACS symptom onset selected from the group consisting of 0-½ hour, ½-1 hour, 1-1½ hours, 1½-2 hours, 2-2½ hours, 2½-3 hours, 0-1 hour, ½-1½ hours, 1-2 hours, and 1½-2½ hours.

In some embodiments, the patient experiences an improvement in progression to myocardial infarction, 30-day survival, in-hospital mortality, or cardiac arrest due to the GIK treatment.

In some embodiments, the patient experiences a significant clinical improvement, or a group of patients experiences a statistically significant improvement, with respect to 30-day survival, 30-day heart failure, or in-hospital cardiac arrest.

In some embodiments, the patient is further treated with aspirin, P2Y12 receptor antagonist (e.g., Clopidogrel (Plavix), Prasugrel (Effient), and Ticagrelor (Brilinta)), anti-coagulant (e.g., Bivalirudin (Angiomax), Enoxaparin (Lovenox), Fondaparinux (Arixtra), and unfractionated heparin); beta blockers (e.g., Carvedilol, oral (Coreg), Metoprolol, IV, Metoprolol, oral (Lopressor)), angiotensin-converting enzyme inhibitors (e.g., Enalapril (Vasotec), Captopril and Lisinopril), angiotensin receptor blocker (e.g., Valsartan (Diovan)), fibrinolytic agents (e.g., Tenecteplase (TNK-tPA), Reteplase (rPA), and Streptokinase), statin (e.g., Atorvastatin (Lipitor), simvastatin, and atorvastatin), morphine, nitroglycerin, oxygen, interventional angioplasty, and surgery.

In some embodiments, the GIK includes 25-35% glucose, 45-55 U/L regular insulin, and 70-90 mEq potassium chloride per liter. In some embodiments, the GIK includes 30% glucose, 50 U/L regular insulin, and 80 mEq of potassium chloride per liter.

In some embodiments, the GIK is administered at a speed of 1 to 2 mL/kg/hour for 10-14 hours. In some embodiments, the GIK is administered at a speed of 1.5 mL/kg/hour for 12 hours.

The invention also provides the use of a composition including a solution of glucose-insulin-potassium (GIK) for the preparation of a medicament for treating, inhibiting, or preventing acute coronary syndromes (ACS) in a patient, wherein administration of the GIK is initiated within 0-3 hours of ACS symptom onset.

The invention additionally provides the use of a composition including a solution of GIK for the preparation of a medicament for treating, inhibiting, or preventing acute coronary syndromes (ACS) in a patient, wherein administration of the GIK is initiated upon assessment by emergency medical service personnel.

In some embodiments, the administration of GIK is initiated upon assessment in (a) the emergency department (ED), (b) the hospital upon cardiac arrest, (c) a medical office setting, or (d) under the care of paramedics in the community.

In some embodiments, the patient has or is at risk of developing one or more ACS symptom selected from the group consisting of: chest pain, angina, radiating pain from the chest to the shoulders, arms, upper abdomen, back, neck, or jaw; nausea or vomiting; indigestion; shortness of breath; heavy sweating; lightheadedness; dizziness; fainting; unusual or unexplained fatigue; and feeling restless or apprehensive.

In some embodiments, the GIK is administered during a time frame from ACS symptom onset selected from the group consisting of 0-½ hour, ½-1 hour, 1-1½ hours, 1½-2 hours, 2-2½ hours, 2½-3 hours, 0-1 hour, ½-1½ hours, 1-2 hours, and 1½-2½ hours.

In some embodiments, the patient experiences an improvement in progression to myocardial infarction, 30-day survival, in-hospital mortality, or cardiac arrest due to the GIK treatment.

In some embodiments, the patient experiences a significant clinical improvement, or a group of patients experiences a statistically significant improvement, with respect to 30-day survival, 30-day heart failure, or in-hospital cardiac arrest.

In some embodiments, the patient is further treated with aspirin, P2Y12 receptor antagonist (e.g., Clopidogrel (Plavix), Prasugrel (Effient), and Ticagrelor (Brilinta)), anticoagulant (e.g., Bivalirudin (Angiomax), Enoxaparin (Lovenox), Fondaparinux (Arixtra), and untractionated heparin); beta blockers (e.g., Carvedilol, oral (Coreg), Metoprolol, IV, Metoprolol, oral (Lopressor)), angiotensin-converting enzyme inhibitors (e.g., Enalapril (Vasotec), Captopril and Lisinopril), angiotensin receptor blocker (e.g., Valsartan (Diovan)), fibrinolytic agents (e.g., Tenecteplase (TNK-tPA), Reteplase (rPA), and Streptokinase), statin (e.g., Atorvastatin (Lipitor), simvastatin, and atorvastatin), morphine, nitroglycerin, oxygen, interventional angioplasty, and surgery.

In some embodiments, the GIK includes 25-35% glucose, 45-55 U/L regular insulin, and 70-90 mEq potassium chloride per liter. In some embodiments, the GIK includes 30% glucose, 50 U/L regular insulin, and 80 mEq of potassium chloride per liter.

In some embodiments, the GIK is administered at a speed of 1 to 2 mL/kg/hour for 10-14 hours. In some embodiments, the GIK is administered at a speed of 1.5 mL/kg/hour for 12 hours.

DETAILED DESCRIPTION

The present invention is based, in part, on the discovery that initiation of administration of glucose-insulin-potassium (GIK) during the time period of 0-3 hours from acute coronary syndromes (ACS) symptom onset provides therapeutic benefits to patients. Accordingly, the invention provides methods for treating ACS and preventing its sequelae by initiating administration of GIK during the time period of 0-3 hours from ACS symptom onset. GIK administration then continues, for example, for about 8-24 hours, e.g., about 12 hours, as determined to be appropriate by those of skill in the art. The invention also provides methods for treating and preventing ACS and its sequelae by immediate administration of GIK upon assessment of a patient by emergency medical service (EMS) or emergency department (ED) personnel.

Treatment according to the methods of invention can result in, for example, the following improvements: prevention of cardiac arrest, limiting of progression of unstable angina pectoris to myocardial infarction, lessening of infarct size, preservation of cardiac left ventricular function, prevention of cardiac arrhythmias, and ultimately decreased morbidity and mortality.

Treatment according to the methods of the invention can be carried out by medical professionals (e.g., paramedics) in communities in out-of-hospital settings (e.g., EMS or ambulance) settings. Alternatively, the methods can be carried out in hospitals (e.g., in the ED, in an intensive care unit, or in an operating room) or in medical office settings.

Patients who can be treated include those diagnosed by assessment of, e.g., patient history, symptoms, electrocardiography, or cardiac biomarkers. For example, patients treated according to the methods of the invention may be those experiencing one or more ACS symptom as described herein. Symptoms of ACS typically arise suddenly and include, for example, chest pain or angina pectoris, which may be characterized by chest aching, pressure, tightness, or burning. Additional ACS symptoms include pain radiating from the chest to the shoulders, arms, upper abdomen, back, neck, or jaw; nausea or vomiting; indigestion; shortness of breath; heavy sweating; lightheadedness; dizziness; fainting; unusual or unexplained fatigue; and feeling restless or apprehensive. These symptoms may appear on their own or in combination and are typically confirmed as representing ACS by doing an electrocardiogram.

According to some methods of the invention, GIK is administered intravenously to patients within 0-3 hours (e.g., within 0-½ hour, ½-1 hour, 1-1½ hours, 1½-2 hours, 2-2½ hours, 2½-3 hours, 0-1 hour, ½-1½ hours, 1-2 hours, or 1½-2½ hours) of symptom onset. In other methods, GIK is administered upon initial assessment by emergency medical services personnel. Such administration typically takes place within minutes (e.g., 1-30, 2-20, or 5-10 minutes) of EMS arrival to the location of an afflicted patients.

In some examples, the GIK solution is as follows: 30% glucose (300 g/L), 50 U/L of regular insulin, and 80 mEq of KCl/L, and is administered intravenously using an infusion pump set at 1.5 mL/kg/h (approximately 100 mL/h for a 70-kg patient) for 12 hours. Variations in this formulation and its administration could also be used analogously, but for the patient's benefit, they would require testing for safety and efficacy. Accordingly, and as is understood in the art, variations of this solution and/or regimen can be used, and still be within the scope of the invention. Thus, for example, the glucose could be present in the solution in the range of 25-35%, or about 30%; the insulin can be present in the amount of 45-55 U/L, or about 50 U/L; and the KCl can be present in the amount of 70-90 mEq, or about 80 m Eq. The speed of the pump can additionally be varied, as can be determined to be appropriate by those of skill in the art, as can the length of administration (e.g., 4-24 hours, 8-20 hours, 10-15 hours, or about 12 hours).

All therapeutic forms of short-acting, regular insulin and its analogs including, for example, branded, generic, branded generic, and biosimilar forms, can be used in the present invention. The invention thus includes the use of Insulin Regular Human (Humulin R, Novolin R, Humulin R U-500) GIK treatment can optionally be carried out in combination with other treatments of ACS. Thus, for example, it can be carried out in combination with any one or more of the following agents or treatments, as determined to be appropriate by those of skill in the art: aspirin, P2Y12 receptor antagonists (e.g., Clopidogrel (Plavix), Prasugrel (Effient), and Ticagrelor (Brilinta)), anticoagulants (e.g., Bivalirudin (Angiomax), Enoxaparin (Lovenox), Fonda-parinux (Arixtra), and unfractionated heparin); beta blockers (e.g., Carvedilol, oral (Coreg), Metoprolol, IV, Metoprolol, oral (Lopressor)), angiotensin-converting enzyme inhibitors (e.g., Enalapril (Vasotec), Captopril and Lisinopril), angiotensin receptor blockers (e.g., Valsartan (Diovan)), fibrin-olytic agents (e.g., Tenecteplase (TNK-tPA), Reteplase (rPA), and Streptokinase), statins (e.g., Atorvastatin (Lipitor), simvastatin, and atorvastatin), morphine, nitroglycerin, oxygen, interventional angioplasty, and surgery.

EXAMPLES

In experimental animal studies, and in some clinical studies, but not, others, GIK has been shown to reduce cardiac arrest, acute myocardial infarction (AMI), and death by substantial amounts—as much as 50% or more for this most common cause of morbidity and mortality. We analyzed the extant literature on this and concluded that timing may be very important. We then did an interventional clinical trial in which GIK reduced cardiac arrest or mortality and myocardial infarct size in patients presenting with acute coronary syndromes (ACS, which includes AMI and unstable angina pectoris) (Selker et al., JAMA 307(18): 1925-1933, 2012). Subsequent detailed analysis of the study data revealed that the optimal effect of GIK on these outcomes is seen if GIK is administered within about three hours of the onset of ACS symptoms. Therefore, the present invention is based on our observation that GIK should be given early, for example, within this time window, which will ensure the best effect, and thereby the best benefit-risk ratio, for the use of GIK.

The table provided below shows data from a clinical trial on the significance on the key outcome of 30-day death or heart failure or in-hospital cardiac arrest by hour periods of administration of GIK from acute coronary syndromes symptom onset. Note that for in the period from 0-3 hours, there is a statistically significant (P value 0.0331) impact for a hazard ratio of 0.52 (i.e., a reduction by 48% in these key outcomes). This is thus a key period for the administration of GIK.

| Outcome: 30-day death or 30-day heart failure or in-hospital cardiac arrest | | | | | | | | |
|---|---|---|---|---|---|---|---|---|
| Outcome: 30-day death or 30-day HF or in-hospital cardiac arrest | GIK | | | Placebo | | | P-values | |
| | | | | | | | GIK vs. | |
| (any3_die_hf_arr_30day) | N | # | % | N | #% | HR (95% CI) | Placebo | Interaction |
| All | 411 | 28 | 6.8% | 460 | 51 | 11.0% | 0.60 (0.38, 0.94) | 0.0266 | n/a |
| Time from onset to study drug start (3 categories_NEW VERSION 1) | | | | | | | | |
| missing | 41 | 4 | 9.8% | 37 | 6 | 16.0% | | | |
| a. 0 to 3 hrs | 251 | 15 | 6.0% | 297 | 33 | 11.0% 0.52 (0.28, 0.95) | 0.0333 | 0.2773 |
| b. 3 to 6 hrs | 46 | 1 | 2.2% | 55 | 5 | 9.1% 0.23 (0.03, 1.92) | 0.1748 | |
| c. over 6 hrs | 73 | 8 | 11.0% | 71 | 7 | 9.9% 1.13 (0.42, 3.08) | 0.8057 | |
| Time from onset to study drug start (4 categories_NEW VERSION 2) | | | | | | | | |
| missing | 41 | 4 | 9.8% | 37 | 6 | 16.0% | | | |
| a. 0 to 1 hrs | 125 | 8 | 6.4% | 141 | 21 | 15.0% 0.40 (0.18, 0.89) | 0.0252 | 0.3224 |
| b. 2 to 3 hrs | 126 | 7 | 5.6% | 156 | 12 | 7.7% 0.72 (0.29, 1.82) | 0.4888 | |
| c. 3 to 6 hrs | 46 | 1 | 2.2% | 55 | 5 | 9.1% 0.23 (0.03, 1.92) | 0.1748 | |
| d. over 6 hrs | 73 | 8 | 11.0% | 71 | 7 | 9.9% 1.13 (0.42, 3.08) | 0.8057 | |
| DER: Categorized time from symptom onset to Trt start [ORIGINAL CATEGORIES IN TRIAL] | | | | | | | | |
| a. 0 to 30 | 24 | 3 | 13.0% | 20 | 2 | 10.0% 1.18 (0.20, 6.96) | 0.8527 | 0.4922 |
| b. 30 to 60 | 101 | 5 | 5.0% | 121 | 19 | 16.0% 0.29 (0.11, 0.78) | 0.0137 | |
| c. 60 to 90 | 60 | 4 | 6.7% | 74 | 5 | 6.8% 1.01 (0.27, 3.74) | 0.9841 | |
| d. 90 to 150 | 52 | 2 | 3.8% | 66 | 5 | 7.6% 0.49 (0.10, 2.48) | 0.3897 | |

| Outcome: 30-day death or 30-day heart failure or in-hospital cardiac arrest | | | | | | | | |
|---|---|---|---|---|---|---|---|---|
| Outcome: 30-day death or 30-day HF or in-hospital cardiac arrest | GIK | | | Placebo | | | P-values GIK vs. | |
| (any3_die_hf_arr_30day) | N | # | % | N | #% | HR (95% CI) | Placebo | Interaction |
| e. 150 to 360 | 60 | 2 | 3.3% | 71 | 7 | 9.9% | 0.33 (0.07, 1.56) | 0.1607 | |
| g. 360 to 24 h | 37 | 5 | 14.0% | 36 | 2 | 5.6% | 2.58 (0.51, 13.19) | 0.2541 | |
| k. >24 hrs | 36 | 3 | 8.3% | 35 | 5 | 14.0% | 0.57 (0.14, 2.32) | 0.4335 | |
| l. Within 24 | 31 | 3 | 9.7% | 34 | 5 | 15.0% | 0.63 (0.15, 2.58) | 0.5182 | |
| m. Missing | 10 | 1 | 10.0% | 3 | 1 | 33.0% | 0.23 (0.01, 3.92) | 0.3108 | |
| NEW: Categorized time from symptom onset to Trt start | | | | | | | | |
| NEW-TIME CATS a. 0 to 30 | 24 | 3 | 13.0% | 20 | 2 | 10.0% | 1.18 (0.20, 6.96) | 0.8527 | 0.4712 |
| b. 30 to 60 | 101 | 5 | 5.0% | 121 | 19 | 16.0% | 0.29 (0.11,0.78) | 0.0137 | |
| c. 60 to 90 | 60 | 4 | 6.7% | 74 | 5 | 6.8% | 1.01 (0.27, 3.74) | 0.9841 | |
| d. 90 to 180 | 66 | 3 | 4.5% | 82 | 7 | 8.5% | 0.52 (0.14, 1.98) | 0.3365 | |
| e. 180 to 360 | 46 | 1 | 2.2% | 55 | 5 | 9.1% | 0.23 (0.03, 1.92) | 0.1747 | |
| g. 360 to 24 h | 37 | 5 | 14.0% | 36 | 2 | 5.6% | 2.58 (0.51, 13.19) | 0.2541 | |
| k. >24 hrs | 36 | 3 | 8.3% | 35 | 5 | 14.0% | 0.57 (0.14, 2.32) | 0.4335 | |
| l. Within 24 | 31 | 3 | 9.7% | 34 | 5 | 15.0% | 0.63 (0.15, 2.58) | 0.5182 | |
| m. Missing | 10 | 1 | 10.0% | 3 | 1 | 33.0% | 0.23 (0.01, 3.92) | 0.3108 | |

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Some embodiments are within the scope of the following numbered paragraphs.

1. A method of treating, inhibiting, or preventing acute coronary syndromes (ACS) in a patient, the method comprising of initiating the administration a solution of glucose-insulin-potassium (GIK) to the patient within 0-3 hours of ACS symptom onset.

2. A method of treating, inhibiting, or preventing acute coronary syndromes (ACS) in a patient, the method comprising of initiating the administration a solution of glucose-insulin-potassium (GIK) to the patient upon assessment by emergency medical service personnel.

3. The method of paragraph 1, wherein the administration of GIK is initiated upon assessment in (a) the emergency department (ED), (b) the hospital upon cardiac arrest, (c) a medical office setting, or (d) under the care of paramedics in the community.

4. The method of any one of paragraphs 1 to 3, wherein the patient has or is at risk of developing one or more ACS symptom selected from the group consisting of: chest pain, angina, radiating pain from the chest to the shoulders, arms, upper abdomen, back, neck, or jaw; nausea or vomiting; indigestion; shortness of breath; heavy sweating; lightheadedness; dizziness; fainting; unusual or unexplained fatigue; and feeling restless or apprehensive.

5. The method of any one of paragraphs 1 to 4, wherein the GIK is administered during a time frame from ACS symptom onset selected from the group consisting of 0-½ hour, ½-1 hour, 1-1½ hours, 1½-2 hours, 2-2½ hours, 2½-3 hours, 0-1 hour, ½-1½ hours, 1-2 hours, and 1½-2½ hours.

6. The method of any one of paragraphs 1 to 5, wherein the patient experiences an improvement in progression to myocardial infarction, 30-day survival, in-hospital mortality, or cardiac arrest due to the GIK treatment.

7. The method of any one of paragraphs 1 to 6, wherein the patient experiences a significant clinical improvement, or a group of patients experiences a statistically significant improvement, with respect to 30-day survival, 30-day heart failure, or in-hospital cardiac arrest.

8. The method of any one of paragraphs 1 to 7, wherein the patient is further treated with aspirin, $P2Y_{12}$ receptor antagonist (e.g., Clopidogrel (Plavix), Prasugrel (Effient), and Ticagrelor (Brilinta)), anticoagulant (e.g., Bivalirudin (Angiomax), Enoxaparin (Lovenox), Fondaparinux (Arixtra), and unfractionated heparin); beta blockers (e.g., Carvedilol, oral (Coreg), Metoprolol, IV, Metoprolol, oral (Lopressor)), angiotensin-converting enzyme inhibitors (e.g., Enalapril (Vasotec), Captopril and Lisinopril), angiotensin receptor blocker (e.g., Valsartan (Diovan)), fibrinolytic agents (e.g., Tenecteplase (TNK-tPA), Reteplase (rPA), and Streptokinase), statin (e.g., Atorvastatin (Lipitor), simvastatin, and atorvastatin), morphine, nitroglycerin, oxygen, interventional angioplasty, and surgery.

9. The method of any one of paragraphs 1 to 8, wherein the GIK comprises 25-35% glucose, 45-55 U/L regular insulin, and 70-90 mEq potassium chloride per liter.

10. The method of paragraph 9, wherein the GIK comprises 30% glucose, 50 U/L regular insulin, and 80 mEq of potassium chloride per liter.

11. The method of any one of paragraphs 1 to 10, wherein the GIK is administered at a speed of 1 to 2 mL/kg/hour for 10-14 hours.

12. The method of paragraph 11, wherein the GIK is administered at a speed of 1.5 mL/kg/hour for 12 hours.

13. A composition comprising a solution of glucose-insulin-potassium (GIK) for use in treating, inhibiting, or preventing acute coronary syndromes (ACS) in a patient, wherein administration of the GIK is initiated within 0-3 hours of ACS symptom onset.

14. A composition comprising a solution of GIK for use in treating, inhibiting, or preventing acute coronary syndromes (ACS) in a patient, wherein administration of the GIK is initiated upon assessment by emergency medical service personnel.

15. The composition for use of paragraph 13, wherein the administration of GIK is initiated upon assessment in (a) the emergency department (ED), (b) the hospital upon cardiac arrest, (c) a medical office setting, or (d) under the care of paramedics in the community.

16. The composition for use of any of one paragraphs 13 to 15, wherein the patient has or is at risk of developing one or more ACS symptom selected from the group consisting of: chest pain, angina, radiating pain from the chest to the shoulders, arms, upper abdomen, back, neck, or jaw; nausea or vomiting; indigestion; shortness of breath; heavy sweating; lightheadedness; dizziness; fainting; unusual or unexplained fatigue; and feeling restless or apprehensive.

17. The composition for use of any one of paragraphs 13 to 16, wherein the GIK is administered during a time frame from ACS symptom onset selected from the group consisting of 0-½ hour, ½-1 hour, 1-1½ hours, 1½-2 hours, 2-2½ hours, 2½-3 hours, 0-1 hour, ½-1½ hours, 1-2 hours, and 1½-2½ hours.

18. The composition for use of any one of paragraphs 13 to 17, wherein the patient experiences an improvement in progression to myocardial infarction, 30-day survival, in-hospital mortality, or cardiac arrest due to the GIK treatment.

19. The composition for use of any one of paragraphs 13 to 18, wherein the patient experiences a significant clinical improvement, or a group of patients experiences a statistically significant improvement, with respect to 30-day survival, 30-day heart failure, or in-hospital cardiac arrest.

20. The composition for use of any one of paragraphs 13 to 19, wherein the patient is further treated with aspirin, $P2Y_{12}$ receptor antagonist (e.g., Clopidogrel (Plavix), Prasugrel (Effient), and Ticagrelor (Brilinta)), anticoagulant (e.g., Bivalirudin (Angiomax), Enoxaparin (Lovenox), Fondaparinux (Arixtra), and unfractionated heparin); beta blockers (e.g., Carvedilol, oral (Coreg), Metoprolol, IV, Metoprolol, oral (Lopressor)), angiotensin-converting enzyme inhibitors (e.g., Enalapril (Vasotec), Captopril and Lisinopril), angiotensin receptor blocker (e.g., Valsartan (Diovan)), fibrolinolytic agents (e.g., Tenecteplase (TNK-tPA), Reteplase (rPA), and Streptokinase), statin (e.g., Atorvastatin (Lipitor), simvastatin, and atorvastatin), morphine, nitroglycerin, oxygen, interventional angioplasty, and surgery.

21. The composition for use of any one of paragraphs 13 to 20, wherein the GIK comprises 25-35% glucose, 45-55 U/L regular insulin, and 70-90 mEq potassium chloride per liter.

22. The composition for use of paragraph 21, wherein the GIK comprises 30% glucose, 50 U/L regular insulin, and 80 mEq of potassium chloride per liter.

23. The composition for use of any one of paragraphs 13 to 22, wherein the GIK is administered at a speed of 1 to 2 mL/kg/hour for 10-14 hours.

24. The composition for use of paragraph 23, wherein the GIK is administered at a speed of 1.5 mL/kg/hour for 12 hours.

25 Use of a composition comprising a solution of glucose-insulin-potassium (GIK) for the preparation of a medicament for treating, inhibiting, or preventing acute coronary syndromes (ACS) in a patient, wherein administration of the GIK is initiated within 0-3 hours of ACS symptom onset.

26. Use of a composition comprising a solution of GIK for the preparation of a medicament for treating, inhibiting, or preventing acute coronary syndromes (ACS) in a patient, wherein administration of the GIK is initiated upon assessment by emergency medical service personnel.

27. The use of paragraph 25, wherein the administration of GIK is initiated upon assessment in (a) the emergency department (ED), (b) the hospital upon cardiac arrest, (c) a medical office setting, or (d) under the care of paramedics in the community.

28. The use of any of one paragraphs 25 to 27, wherein the patient has or is at risk of developing one or more ACS symptom selected from the group consisting of: chest pain, angina, radiating pain from the chest to the shoulders, arms, upper abdomen, back, neck, or jaw; nausea or vomiting; indigestion; shortness of breath; heavy sweating; lightheadedness; dizziness; fainting; unusual or unexplained fatigue; and feeling restless or apprehensive.

29. The use of any one of paragraphs 25 to 28, wherein the GIK is administered during a time frame from ACS symptom onset selected from the group consisting of 0-½ hour, ½-1 hour, 1-1½ hours, 1½-2 hours, 2-2½ hours, 2½-3 hours, 0-1 hour, ½-1½ hours, 1-2 hours, and 1½-2½ hours.

30. The use of any one of paragraphs 25 to 29, wherein the patient experiences an improvement in progression to myocardial infarction, 30-day survival, in-hospital mortality, or cardiac arrest due to the GIK treatment.

31. The use of any one of paragraphs 25 to 30, wherein the patient experiences a significant clinical improvement, or a group of patients experiences a statistically significant improvement, with respect to 30-day survival, 30-day heart failure, or in-hospital cardiac arrest.

32. The use of any one of paragraphs 25 to 31, wherein the patient is further treated with aspirin, $P2Y_{12}$ receptor antagonist (e.g., Clopidogrel (Plavix), Prasugrel (Effient), and Ticagrelor (Brilinta)), anticoagulant (e.g., Bivalirudin (Angiomax), Enoxaparin (Lovenox), Fondaparinux (Arixtra), and unfractionated heparin); beta blockers (e.g., Carvedilol, oral (Coreg), Metoprolol, IV, Metoprolol, oral (Lopressor)), angiotensin-converting enzyme inhibitors (e.g., Enalapril (Vasotec), Captopril and Lisinopril), angiotensin receptor blocker (e.g., Valsartan (Diovan)), fibrolinolytic agents (e.g., Tenecteplase (TNK-tPA), Reteplase (rPA), and Streptokinase), statin (e.g., Atorvastatin (Lipitor), simvastatin, and atorvastatin), morphine, nitroglycerin, oxygen, interventional angioplasty, and surgery.

33. The use of any one of paragraphs 25 to 32, wherein the GIK comprises 25-35% glucose, 45-55 U/L regular insulin, and 70-90 mEq potassium chloride per liter.

34. The use of paragraph 33, wherein the GIK comprises 30% glucose, 50 U/L regular insulin, and 80 mEq of potassium chloride per liter.

35. The use of any one of paragraphs 25 to 34, wherein the GIK is administered at a speed of 1 to 2 mL/kg/hour for 10-14 hours.

36. The use of paragraph 35, wherein the GIK is administered at a speed of 1.5 mL/kg/hour for 12 hours.

Other embodiments are within the scope of the following claims.

The invention claimed is:

1. A method of treating, inhibiting, or preventing acute coronary syndromes (ACS) in a patient, the method comprising initiating the administration of a solution of glucose-insulin-potassium (GIK) to the patient within one hour or less of ACS symptom onset.

2. The method of claim 1, further comprising assessment by emergency medical service personnel.

3. The method of claim 1, wherein the administration of GIK is initiated upon assessment in (a) the emergency department (ED), (b) the hospital upon cardiac arrest, (c) a medical office setting, or (d) under the care of paramedics in the community.

4. The method of claim 1, wherein the patient has or is at risk of developing one or more ACS symptom selected from the group consisting of: chest pain, angina, radiating pain from the chest to the shoulders, arms, upper abdomen, back, neck, or jaw; nausea or vomiting; indigestion; shortness of breath; heavy sweating; lightheadedness; dizziness; fainting; unusual or unexplained fatigue; and feeling restless or apprehensive.

5. The method of claim 1, wherein the patient experiences an improvement in progression to myocardial infarction, 30-day survival, in-hospital mortality, or cardiac arrest due to the GIK treatment.

6. The method of claim 1, wherein the patient experiences a significant clinical improvement, or a group of patients experiences a statistically significant improvement, with respect to 30-day survival, 30-day heart failure, or in-hospital cardiac arrest.

7. The method of claim 1, wherein the patient is further treated with aspirin, $P2Y_{12}$ receptor antagonist, anticoagulant, beta blockers, angiotensin-converting enzyme inhibitors, angiotensin receptor blocker, fibrinolytic agent, statin, morphine, nitroglycerin, oxygen, interventional angioplasty, surgery or any combination thereof.

8. The method of claim 1, wherein the GIK comprises 25-35% glucose, 45-55 U/l regular insulin, and 70-90 mEq potassium chloride per liter.

9. The method of claim 8, wherein the GIK comprises 30% glucose, 50 U/l regular insulin, and 80 mEq of potassium chloride per liter.

10. The method of claim 1, wherein the GIK is administered at a speed of 1 to 2 ml/kg/hour for 10-14 hours.

11. The method of claim 10, wherein the GIK is administered at a speed of 1.5 ml/kg/hour for 12 hours.

12. A method of treating, inhibiting, or preventing acute coronary syndromes (ACS) in a patient, the method comprising initiating the administration of a solution of glucose-insulin-potassium (GIK) to the patient within 3 to 6 hours of ACS symptom onset.

13. The method of claim 12, further comprising assessment by emergency medical service personnel.

14. The method of claim 12, wherein the administration of GIK is initiated upon assessment in (a) the emergency department (ED), (b) the hospital upon cardiac arrest, (c) a medical office setting, or (d) under the care of paramedics in the community.

15. The method of claim 12, wherein the patient has or is at risk of developing one or more ACS symptom selected from the group consisting of: chest pain, angina, radiating pain from the chest to the shoulders, arms, upper abdomen, back, neck, or jaw; nausea or vomiting; indigestion; shortness of breath; heavy sweating; lightheadedness; dizziness; fainting; unusual or unexplained fatigue; and feeling restless or apprehensive.

16. The method of claim 12, wherein the patient experiences an improvement in progression to myocardial infarction, 30-day survival, in-hospital mortality, or cardiac arrest due to the GIK treatment.

17. The method of claim 12, wherein the patient experiences a significant clinical improvement, or a group of patients experiences a statistically significant improvement, with respect to 30-day survival, 30-day heart failure, or in-hospital cardiac arrest.

18. The method of claim 12, wherein the patient is further treated with aspirin, $P2Y_{12}$ receptor antagonist, anticoagulant, beta blockers, angiotensin-converting enzyme inhibitors, angiotensin receptor blocker, fibrinolytic agent, statin, morphine, nitroglycerin, oxygen, interventional angioplasty, surgery or any combination thereof.

19. The method of claim 12, wherein the GIK comprises 25-35% glucose, 45-55 U/l regular insulin, and 70-90 mEq potassium chloride per liter.

20. The method of claim 19, wherein the GIK comprises 30% glucose, 50 U/l regular insulin, and 80 m Eq of potassium chloride per liter.

21. The method of claim 12, wherein the GIK is administered at a speed of 1 to 2 ml/kg/hour for 10-14 hours.

22. The method of claim 21, wherein the GIK is administered at a speed of 1.5 ml/kg/hour for 12 hours.

* * * * *